(12) United States Patent
Chapman et al.

(10) Patent No.: US 10,398,870 B2
(45) Date of Patent: *Sep. 3, 2019

(54) SYSTEM AND METHOD OF CONTROLLING THE DELIVERY OF MEDICAL GASES TO A PATIENT

(71) Applicant: General Electric Company, Schenectady, NY (US)

(72) Inventors: Philip E. Chapman, Oregon, WI (US); Robert Q. Tham, Middleton, WI (US); Michael Foulis, Madison, WI (US); Wesley Moreau, Cottage Grove, WI (US)

(73) Assignee: General Electric Company, Schenectady, NY (US)

( * ) Notice: Subject to any disclaimer, the term of this patent is extended or adjusted under 35 U.S.C. 154(b) by 953 days.

This patent is subject to a terminal disclaimer.

(21) Appl. No.: 14/950,849

(22) Filed: Nov. 24, 2015

(65) Prior Publication Data

US 2016/0121070 A1 May 5, 2016

Related U.S. Application Data

(63) Continuation of application No. 13/542,858, filed on Jul. 6, 2012, now Pat. No. 9,233,218, which is a (Continued)

(51) Int. Cl.
*A61M 16/00* (2006.01)
*A61M 16/12* (2006.01)
(Continued)

(52) U.S. Cl.
CPC ........ *A61M 16/12* (2013.01); *A61M 16/0045* (2013.01); *A61M 16/0051* (2013.01);
(Continued)

(58) Field of Classification Search
CPC ...... A61M 16/0051; A61M 2202/0208; A61M 2202/0291; A61M 16/18; A61M 2205/52;
(Continued)

(56) References Cited

U.S. PATENT DOCUMENTS

| 4,266,573 A | 5/1981 | Braatz |
| 6,041,777 A | 3/2000 | Faithfull et al. |

(Continued)

FOREIGN PATENT DOCUMENTS

| CN | 101121051 A | 2/2008 |
| CN | 101310786 A | 11/2008 |

(Continued)

OTHER PUBLICATIONS

Unofficial translation of Chinese Office Action issued in connection with CN Application No. 201310281147.8 dated Apr. 6, 2016.

(Continued)

*Primary Examiner* — Steven O Douglas
(74) *Attorney, Agent, or Firm* — Andrus Intellectual Property Law, LLP (57) ABSTRACT

A system for controlling the delivery of medical gases includes a digital signal processor that receives at least one ventilation parameter value change, calculates a fresh oxygen flow rate, total fresh gas flow rate into the breathing circuit, and a reference oxygen flow rate representative of a predetermined oxygen concentration delivered to a patient. A graphical display presents the calculated fresh oxygen flow rate, total fresh gas flow rate, and reference oxygen flow rate. A method of controlling the delivery of medical gases to a patient includes calculating a total fresh gas flow rate into the breathing circuit, calculating a fresh oxygen flow rate into the breathing circuit, calculating a reference oxygen flow rate representative of a predetermined oxygen concentration delivered to the patient and presenting the (Continued)

total fresh gas flow rate, the fresh oxygen flow rate, and reference oxygen flow rate on a graphical display.

20 Claims, 4 Drawing Sheets

Related U.S. Application Data continuation-in-part of application No. 12/987,544, filed on Jan. 10, 2011, now Pat. No. 8,770,192.

(51) Int. Cl.

| | | |
|---|---|---|
| *A61M 16/01* | (2006.01) | |
| *A61M 16/18* | (2006.01) | |
| *A61M 16/08* | (2006.01) | |
| *A61M 16/20* | (2006.01) | |
| *A61M 16/22* | (2006.01) | |
| *A61M 16/10* | (2006.01) | |

(52) U.S. Cl.
CPC ........ *A61M 16/0057* (2013.01); *A61M 16/01* (2013.01); *A61M 16/0891* (2014.02); *A61M 16/122* (2014.02); *A61M 16/125* (2014.02); *A61M 16/18* (2013.01); *A61M 16/209* (2014.02); *A61M 16/208* (2013.01); *A61M 16/22* (2013.01); *A61M 2016/1025* (2013.01); *A61M 2016/1035* (2013.01); *A61M 2202/025* (2013.01); *A61M 2202/0208* (2013.01); *A61M 2202/0241* (2013.01); *A61M 2202/0283* (2013.01); *A61M 2202/0291* (2013.01); *A61M 2205/18* (2013.01); *A61M 2205/3334* (2013.01); *A61M 2205/50* (2013.01); *A61M 2205/502* (2013.01); *A61M 2205/505* (2013.01); *A61M 2205/52* (2013.01)

(58) Field of Classification Search
CPC ...... A61M 16/0045; A61M 2202/0241; A61M 2205/18; A61M 2202/0283; A61M 16/0891; A61M 16/122; A61M 16/209
See application file for complete search history.

(56) References Cited

U.S. PATENT DOCUMENTS

| | | |
|---|---|---|
| 6,523,537 B1 | 2/2003 | Mas Marfany |
| 6,619,289 B1 | 9/2003 | Mashak |
| 6,725,860 B2 | 4/2004 | Wallroth et al. |
| 6,828,910 B2 | 12/2004 | Vanryzin et al. |
| 7,305,988 B2 | 12/2007 | Acker et al. |
| 7,334,578 B2 | 2/2008 | Biondi et al. |
| 7,556,036 B2 | 7/2009 | Bouillon et al. |
| 7,762,255 B2 | 7/2010 | Mills |
| 8,770,192 B2* | 7/2014 | Tham ................ A61M 16/0045 128/204.21 |
| 9,233,218 B2* | 1/2016 | Chapman .......... A61M 16/0045 |
| 2002/0017296 A1 | 2/2002 | Hickle |
| 2002/0148471 A1 | 10/2002 | Hirabayashi |
| 2007/0000494 A1 | 1/2007 | Banner et al. |
| 2007/0173729 A1 | 7/2007 | Fisher et al. |
| 2007/0181126 A1 | 8/2007 | Tolmie et al. |
| 2008/0029092 A1 | 2/2008 | Heesch |
| 2009/0205654 A1 | 2/2009 | Bouillon et al. |
| 2012/0174926 A1 | 7/2012 | Tham |

FOREIGN PATENT DOCUMENTS

| | | |
|---|---|---|
| CN | 101500633 A | 8/2009 |
| EP | 0835672 A2 | 4/1998 |
| EP | 0894506 A2 | 2/1999 |
| EP | 0911052 A2 | 4/1999 |
| EP | 1072279 A1 | 1/2001 |
| EP | 2474334 A1 | 7/2012 |
| WO | 2007033271 A1 | 3/2007 |
| WO | 2010033439 A2 | 3/2010 |

OTHER PUBLICATIONS

Anesthesia Workstations Brochure, Draeger Medical, Inc.; Copyrighted 2011.

Baum, Jan A. "Low Flow Anaesthesia: The Theory and Practice of Low Flow, Minimal Flow and Closed System Anaesthesia", Published by Butterworth-Heinemann on Apr. 12, 1996 ISBN 0750621273 pp. 40-45.

Takafumi Azami, et al. "Calculation of 02 Consumption During Low-Flow Anesthesia from Tidal Gas Concentrations, Flowmeter, and Minute Ventilation", Journal of Clinical Monitoring and Computing, Kluwer Academic Publishers, DO, vol. 18, No. 5-6, Dec. 1, 2004, pp. 325-332.

Tsai-Hsin Chen, et al. "The Relations Between Oxygen Consumption and the Equilibrated Inspired Oxygen Fraction in an Anesthetic Circle Breathing System: A Mathematic Formulation & Laboratory Simulations", Annals of Biomedical Engineering, vol. 37, No. 1, Jan. 1, 2009, pp. 246-254.

Search Report and Written Opinion from EP Application No. 12150356.9 dated Apr. 23, 2012.

Search Report and Written Opinion from EP Application No. 13174980.6 dated Nov. 7, 2013.

Search Report and Written Opinion from EP Application No. 13174980.6 dated Feb. 25, 2014.

Unofficial translation of Chinese Office Action issued in connection with CN Application No. 201210020320.4 dated Feb. 16, 2015.

\* cited by examiner

SYSTEM AND METHOD OF CONTROLLING THE DELIVERY OF MEDICAL GASES TO A PATIENT

CROSS REFERENCE TO RELATED APPLICATION

This application is continuation of U.S. application Ser. No. 13/542,858, filed Jul. 6, 2012, which application was published on Nov. 1, 2012, as U.S. Publication No. US20120272957, which application is a continuation-in-part of U.S. application Ser. No. 12/987,544, filed Jan. 10, 2011, which application was granted on Jul. 8, 2014, as U.S. Pat. No. 8,770,192, which applications are incorporated herein by reference in their entireties.

BACKGROUND

The present disclosure is related to the field of mechanical ventilation. More specifically, the current disclosure is related to the prevention of the delivery of hypoxic gases to a patient.

Known guards against the delivery of hypoxic gases are based upon minimum concentration settings to ensure the addition of adequate fresh gas oxygen to a breathing circuit. Such a minimum concentration setting is maintained with a mechanical or equivalent link between the gas flow settings of the constituent gases of the delivered fresh gas. Such linkages ensure that the resulting mixture of fresh gas maintains a required minimum oxygen concentration.

During some mechanical ventilator operational settings, particularly low flow mechanical ventilator operation, hypoxic gases can still be delivered to a patient, even when known hypoxic guards register that the minimum oxygen concentration for fresh gas flows has been met.

BRIEF DISCLOSURE

A system for controlling the delivery of medical gases during respiratory support of a patient includes a breathing circuit with a patient connection configured to deliver respiratory support to the patient. A mixer is pneumatically connected to the breathing circuit. The mixer is configured to provide at least oxygen and a balance gas to the breathing circuit. A mechanical ventilator is pneumatically connected to the breathing circuit and is configured to create fluid pressure waveforms within the breathing circuit to provide respiratory support to the patient. A digital signal processor is communicatively connected to the mixer and the mechanical ventilator. The digital signal processor receives at least one ventilation parameter value change, calculates a fresh oxygen flow rate into the breathing circuit and total fresh gas flow rate into the breathing circuit with the at least one ventilation parameter value. The digital signal processor calculates a reference oxygen flow rate representative of a predetermined oxygen concentration delivered to the patient with at least the total fresh gas flow rate. A graphical display is communicatively connected to the digital signal processor. The graphical display presents the calculated fresh oxygen flow rate, the total fresh gas flow rate, and the reference oxygen flow rate.

A low-flow ventilation system provides repeating breaths of respiratory support to a patient. The low-flow ventilation system includes a breathing circuit with a patient connection configured to deliver the respiratory support to the patient. An input device is operable by a clinician to input at least one ventilation parameter value. A mixer is pneumatically connected to the breathing circuit and is configured to provide at least oxygen and a balance gas to the breathing circuit. A vaporizer is pneumatically connected to the breathing circuit and to the mixer. The vaporizer receives at least the oxygen and the balance gas from the mixer and entrains anesthetic agent vapor into the received oxygen and balance gas. A digital signal processor is communicatively connected to the input device. The digital signal processor receives the at least one ventilation parameter value, calculates a fresh oxygen flow rate into the breathing circuit, calculates a total fresh gas flow rate into the breathing circuit, calculates a predicted oxygen concentration delivered to the patient, and compares the predicted oxygen concentration to a predetermined minimum oxygen requirement threshold of the patient. A graphical display is communicatively connected to the digital signal processor and presents the calculated fresh oxygen flow rate and total fresh gas flow rate. If the predicted oxygen concentration is above the predetermined minimum oxygen requirement threshold, the digital signal processor accepts the at least one ventilation parameter value.

A method of controlling the delivery of medical gases to a patient receiving ventilatory support from a low-flow mechanical ventilator includes providing respiratory support to the patient through a breathing circuit pneumatically connected to a mechanical ventilator in a low-flow configuration. A flow of medical gas comprising oxygen is received with a mixer pneumatically connected to the breathing circuit. A ventilation parameter value change is received with a digital signal processor. A total fresh gas flow rate into the breathing circuit is calculated with the digital signal processor from the received ventilation parameter value change. A fresh oxygen flow rate into the breathing circuit is calculated with the digital signal processor from the received ventilation parameter value change. A reference oxygen flow rate is calculated with the digital signal processor. The reference oxygen flow rate achieves a predetermined oxygen concentration as delivered to the patient based upon the total fresh gas flow rate. The total fresh gas flow rate, the fresh oxygen flow rate and reference oxygen flow rate are presented on a graphical display.

DETAILED DISCLOSURE

Figure 1:
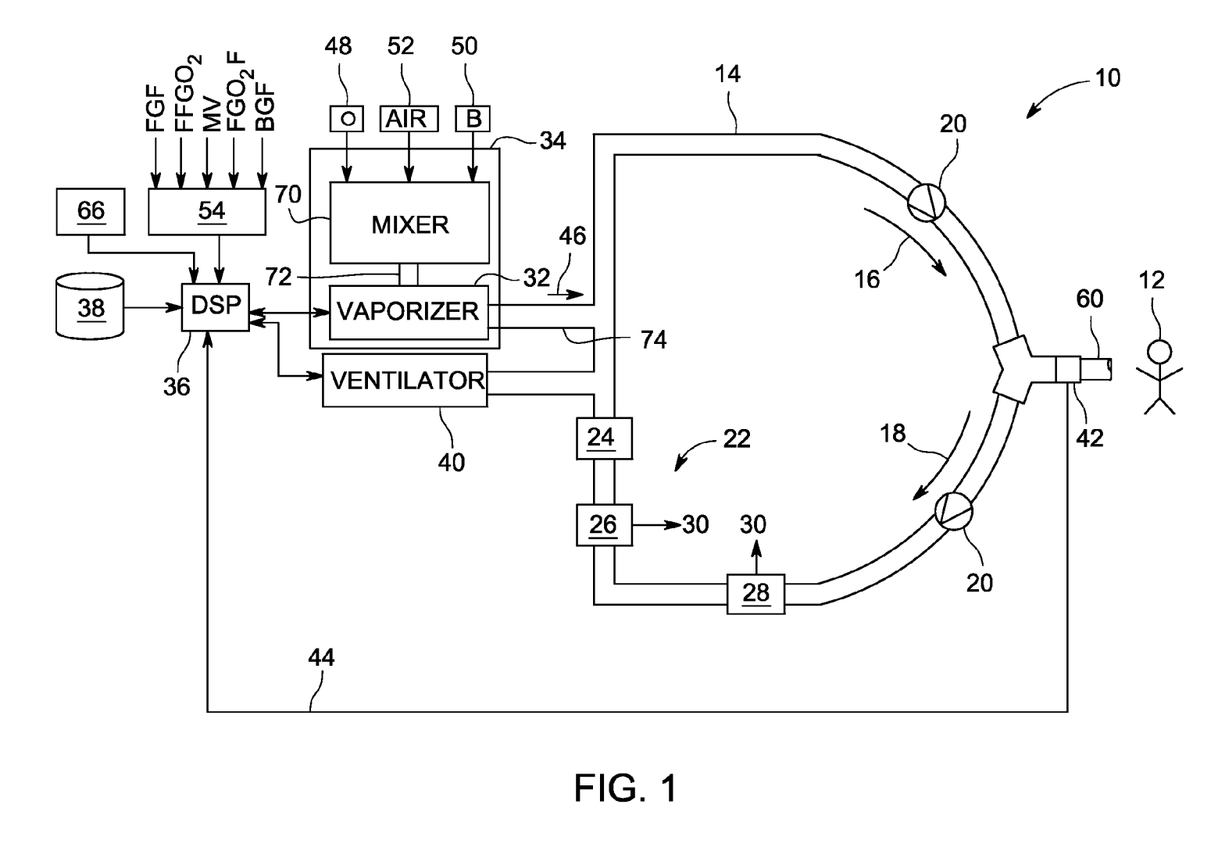
FIG. 1 is a schematic diagram of an embodiment of a low-flow ventilation system.

FIG. 1 is a schematic diagram of a system 10 for providing respiratory support to a patient 12 while preventing the delivery of hypoxic gases to the patient 12.

A respiratory support system 10 includes a breathing circuit 14 through which inspiratory gases 16 are provided to the patient and expired gases 18 are directed from the patient 12. Check valves 20 within the breathing circuit 14 ensure the unidirectional flow of gas within the breathing circuit 14.

In a high flow respiratory support system most or all of the expired gases 18 are vented, exemplarily through relief valve 26, to the ambient air.

In low flow respiratory support system, gases are added and removed from the breathing circuit 14. Attributed to metabolism, the patient 12 adds carbon dioxide and removes oxygen from the breathing circuit 14. During expiration, the expired gases 18 are directed to an absorber 24 where the carbon dioxide produced by the patient 12 is removed. Some small amount of gas 28 (less than 0.3 liters per min) is leaked from the breathing circuit 14. The remaining expired gas volume is stored in the ventilator 40 to be kept in reserve for the next tidal breath. To make up for the loss of gases by the patient 12 and leaks 28, fresh gas 46 is added to the breathing circuit. Typically the fresh gas 46 is added (about 0.5 to 3 liters per min) in excess of the total gas loss and forces the removal of some of the expired gas 18 through a relief valve 26. Concentration of gases from the relief valve 26 have approximately the same concentration as the patient expired gases. The ventilator 40 delivers the next tidal breath by compressing the remaining reserve volume. The unidirectional check valves 20 control the direction of gas flow in the breathing circuit 14 for the inspiratory gases 16 going to the patient 12 and expired gases 18 from the patient 12.

In this embodiment, the fresh gas 46 comes from the fresh gas manifold 34. The fresh gas 46 comprises at least two medical gases from a mixer 70 and/or an anesthetic vapor from an anesthetic vaporizer 32. The mixer 70 receives flows of two or more medical gases. The flow rate of the constituent medical gases into the mixer are controlled to create a combined medical gas with a set concentration of constituent medical gases. Often a combination of individual gas (for example oxygen) concentration and total flow rate or individual gas flow rates are used to control the flow of medical gas into the mixer. These mixer control settings can also be interchangeably calculated and used.

Fresh gas from the mixer 70 is provided through conduit 72 to the anesthetic vaporizer 32. In the vaporizer 32, a portion of the gas is diverted through a sump (not depicted) of the vaporizer 32 to serve as a carrier gas to pick up an amount of saturated anesthetic vapor according to the concentration settings of the vaporizer 32. All the gases from the mixer 70 and the anesthetic vapor from the vaporizer 32 are pneumatically conducted as fresh gas 46 via conduit 74 to the breathing circuit 14.

In another embodiment, the anesthetic vaporizer 32 directly injects the required anesthetic vapor into the breathing circuit 14 via conduit 74. Since no carrier gas is required to pick up the anesthetic vapor, the gases from mixer 70 is added directly to the breathing circuit 14 by rerouting the outlet of conduit 72 from the anesthetic vaporizer 32 to the breathing circuit 14 (not shown). Conceptually the replacement fresh gas 46 from the fresh gas manifold 34 consists all of the gases and vapor in the conduits 72 and 74.

A normal range of oxygen concentration inspired by the patient 12 is between 21% and 30%. A normal range of an oxygen concentration in gases expired by the patient 12 is between 17% and 25%.

Therefore, under normal conditions, the expired breathing gases may contain an oxygen concentration of 17% which is only 80% of the minimum required oxygen concentration (21%) to be recirculated to the patient. In high fresh gas flow respiratory support systems, this is not a problem as the fresh gas is held at a minimum oxygen concentration of 21% with current hypoxic guards. However, in a low-flow system, even though the gas loss 26, 28 in the respiratory support system is small and this requires only a small amount of replacement fresh gas, the effect of this gas loss on the required composition of the fresh gas is significant. Under these conditions, even though the minimum gas concentration level (e.g. 21%) at the fresh gas manifold 34 is met, the small volume of fresh gas is insufficient to raise the oxygen concentration of the inspired gases 16 delivered to the patient to the minimum oxygen concentration (e.g. 21%) required by the patient.

Additionally, the patient 12 may require a greater concentration of oxygen due to the physiological condition of the patient 12. In these instances, while the patient 12 may be delivered a technically non-hypoxic gas mixture for the normal population, the inspired gases delivered to the patient 12 may be effectively hypoxic for the oxygen concentration requirements of that specific patient 12.

Therefore, the presently disclosed systems and methods control the provision of fresh gas through the fresh gas manifold 34 in order to prevent the delivery of hypoxic gases to the patient 12.

A digital signal processor (DSP) 36 is communicatively connected to the fresh gas manifold 34 and to the anesthetic vaporizer 32, if one is used. The DSP 36 is further communicatively connected to a computer readable medium 38 that is programmed with computer readable code that upon execution by the DSP 36 causes the DSP 36 to operate in the manner described herein and perform the functions as described herein. The computer readable medium 38 may be any of a variety of configurations of non-volatile memory. In one embodiment, the computer readable medium 38 is an integral part of the DSP 36. In an alternative embodiment, the computer readable medium is a separate component that is communicatively connected to the DSP 36. In one non-limiting embodiment, the computer readable medium 38 is flash memory.

The DSP 36 is connected to a mechanical ventilator 40. The mechanical ventilator 40 is operated by the DSP 36 in order to provide repeating waveforms or breaths of inspired gas 16 to the patient 12. The mechanical ventilator 40 is operated by the DSP 36 to provide a variety of forms of respiratory support, including full ventilation or spontaneous breathing assistance.

A respiratory gas monitor 42 is disposed in or near conduit 60 that is the common y-piece of the breathing circuit 14. The respiratory gas monitor 42 analyzes at least the concentration of the inspired gases 16 flowing into the patient 12 and the expired gases 18 flowing away from the patient 12. The respiratory gas monitor 42 provides a signal 44 that is indicative of the gas concentrations, particularly the oxygen concentration. In still further embodiments, the respiratory gas monitor 42 can provide a signal indicative of inspired and expired anesthetic gas concentrations. The respiratory gas monitor 42 further includes a flow sensor such that the DSP 36 is provided with an indication of the flow of gas to and from the patient 12. The DSP 36 receives the measurements of concentration and flow of gas breathed by the patient 12 and uses this information in determining the amount of fresh gas 46 to be introduced to the breathing circuit 14 from the fresh gas manifold 34.

In an alternative embodiment, gas monitors supplemental to, or in replace of, the respiratory gas monitor 42 are used within the breathing circuit 14. Non limiting examples of such gas monitors include an inspiratory gas monitor (not depicted) disposed within the inspiratory limb, or an expiratory gas monitor (not depicted) disposed within the expiratory limb. In addition to these exemplary sensor configurations, alternative suitable configurations would be recognized by a person of ordinary skill in the art.

The mixer 70 of the fresh gas manifold 34 is connected to one or more sources of medical gas, such as oxygen, nitrous oxide, medical air, heliox, xenon, helium. In practice, the fresh gas manifold 34 is at least connected to an oxygen source 48 and a balance gas source 50. In an alternative embodiment, the fresh gas manifold 34 is connected to an air source. As atmospheric air approximately comprises 21% oxygen and 78% nitrogen, this is a common source of medical gas used with a fresh gas manifold 34 as the concentration of oxygen in the atmospheric air generally meets the minimum hypoxic guard concentrations as discussed above.

An example will highlight differences between previous systems and the systems and methods as disclosed herein. If a normal minute volume of respiratory support to a patient 12 is five liters per minute, then at a minimum oxygen concentration of 21%, the minute volume of oxygen provided to the patient is 1.05 liters per minute. If the gas expired by the patient with metabolic oxygen consumption of 0.2 liters per minute has an oxygen concentration of 17% and 1 liter of gas is lost through the recirculation of the expired gases, then a 17% concentration of oxygen of the 4 liters per minute of recirculated gases will contribute 0.68 liters per minute to the rebreathed inspired gases. Therefore, if 1 liter of fresh gas at 25% oxygen concentration is provided by the fresh gas manifold 34 to replace the lost volume of breathing gases, the minute volume of oxygen in the combined fresh gas and recirculated gas provided as inspiratory gases 16 will only be 0.93 liters per minute or 18.6% oxygen concentration which would be considered a hypoxic mixture and is insufficient to replenish the inspired gas concentration that started at 21%. This shows how the known hypoxic guards at a minimum concentration of 25% can allow hypoxic gas concentrations of less than 21% oxygen to be delivered to the patient.

Rather, in the system 10 disclosed herein, the DSP 36 operates the mixer 70 and fresh gas manifold 34 in a manner such as to control the concentration and flow of the fresh gas 46 provided to the breathing circuit 14, based upon the metabolic needs of the patient 12.

The DSP 36 uses a variety of equations in calculating the characteristics of the fresh gas 46 provided to the breathing circuit 14. Equation (1) generally describes the relationship between the fresh gas 46 delivered from the fresh gas manifold 34 and the oxygen concentration requirements of the patient 12 and can be derived based on the conservation of mass at a steady temperature and pressure.

$$FGO_2F = \dot{V}O_2 + FeO_2(FGF - \dot{V}O_2) \tag{1}$$

In the above equation, the fresh oxygen flow, $FGO_2F$, is the oxygen flow rate in the fresh gas. $\dot{V}O_2$ is the oxygen uptake rate of the patient. $FeO_2$ is the fractional expired oxygen, which is otherwise known as the concentration of oxygen in the expired gases 18. FGF is the total fresh gas flow rate, or the flow rate of the fresh gas 46 provided out of the fresh gas manifold 34. This equation assumes that all the CO2 produced by the patient is completely removed by the carbon dioxide absorber 24. A small correction factor using the fraction of the expired carbon dioxide (typically less than 5 or 6%) can be included to correct the second term in equation 1 to account for the carbon dioxide loss through the relief valve 28 instead of preferentially absorbed by the carbon dioxide absorber 24. The exposure of carbon dioxide to the absorber 24 varies with the location of the absorber 24 and the excess gas relief valve 26. It is also known that if the fresh gas 46 is introduced between the inspiratory unidirection valve and the patient (not shown), the gases lost through the relief valve 26 will include inspiratory gases and more oxygen from the fresh gas is required to ensure non-hypoxic gases delivered to the patient.

In embodiments that do not include a vaporizer, the FGF will be just as described above. However, in embodiments that include a vaporizer 32 in the fresh gas manifold 34, the FGF also includes the anesthetic agent vapor flow (AVF). The vaporizer 32 operates to entrain anesthetic agent vapor into the flow of oxygen and balance gas provided through the vaporizer. In a system that uses a mechanical vaporizer, the AVF is an estimate computed using a measurement of the fraction of agent inspired (FiA) as may be measured by a gas monitor disposed within the breathing circuit. The AVF is calculated using the following equation:

$$AVF(\text{L/min}) = \frac{MGF \times FiA}{1 - FiA} \tag{2}$$

In the above equation, the MGF is the total gas flow provided from the mixer, therefore MGF can also be represented by the equation:

$$MGF = BGF + FGO_2F \tag{3}$$

While equation (1) is written with respect to the fractional expired oxygen, in consideration of the conservation of oxygen breathed over a patient breath, the fractional expired oxygen ($FeO_2$) is related to fractional inspired oxygen ($FiO_2$) by the following equation:

$$FiO_2 = FeO_2 + \frac{\dot{V}O_2}{MV} \tag{4}$$

In equation (2), $FiO_2$ is the fractional inspired oxygen, or the concentration of oxygen in the inspiratory gases 16 provided to the patient 12. MV is the minute volume of total gases that are provided to the patient 12 by the respiratory support system 10. The minute volume may be set by a clinician by entering the minute volume into an input device 54. The minute volume is provided by the input device 54 to the DSP 36, and the DSP 36 operates the ventilator 40 to provide respiratory support to the patient 12 that achieves the established minute volume. The MV can also be measured using the respiratory gas monitor 42. The respiratory gas monitor 42 communicates with DSP 36 via connection 44.

One or more ventilation parameter values of the system 10 are controlled by the clinician, such as by inputs into the input device 54. The DSP 36 manages these input ventilation parameter values using equation (1) such that the clinician does not unknowingly establish a combination of values that will result in a hypoxic gas mixture being delivered to the patient 12. In an exemplary embodiment, one or more of the fresh gas flow rate (FGF), the fractional fresh gas oxygen ($FFGO_2$), and the fresh gas oxygen flow rate ($FGO_2F$) are ventilation parameter values that can be controlled by the clinician.

Additionally, the patient oxygen uptake rate ($\dot{V}O_2$) can be obtained in several ways. The oxygen uptake can be measured from the patient by comparing the volume of oxygen inspired and expired by the patient over a breath. In particular, the oxygen uptake is the integral of the instantaneous product of the oxygen concentration and gas flow breathed by the patient over a breath. This oxygen concentration and gas flow is measured by the respiratory gas monitor 42. With the availability of these measurements, some respiratory gas monitors perform the oxygen uptake computation. Alternatively, these measurements can be fed via the signal 44 to the DSP 36 to compute the integration. An estimation of the oxygen uptake can be obtained by multiplying the difference between $FiO_2$ and $FeO_2$ by the MV. In an embodiment, the respiratory gas monitor 42 measures the $FiO_2$, $FeO_2$ and MV.

In another embodiment, the oxygen uptake rate may be entered by a clinician through the input device 54 as a clinical judgment or estimation based upon patient demographics. In one example, the oxygen uptake rate can be estimated using the patient's weight and the Brody equation. The DSP 36 calculates the oxygen uptake rate from the inspired oxygen concentration and the expired oxygen concentration using equation (2).

In still further embodiments, the oxygen uptake rate can be crudely estimated based upon safe population base values. This can be assumed to be the easiest, but the least accurate as there is a wide range of population need (e.g. 300 milliliters per minute or more for an adult with a fever, or less than 20 milliliters per minute in a neonate). The relationship of the fresh gas oxygen concentration to the fresh gas flow rate and the fresh gas oxygen flow rate are shown below in equations (3) and (4):

$$FFGO_2 = \frac{FGO_2F}{FGF} \quad (5)$$

$$FGF = \frac{FGO_2F}{FFGO_2} \quad (6)$$

Delivery of fresh gas oxygen and a balance gas requires two parameters to control the fresh gas manifold 34. The complementary pairs can be chosen from the concentration of one of the gases and the total fresh gas flow, or the flow of each individual gas. Two commonly used combinations of these complementary setting pairs are $FFGO_2$ and $FGF$, or $FGO_2F$ and a balance gas flow rate (BGF). In one embodiment of the disclosed hypoxic guard, the $FGO_2F$ or the $FGF$ is derived using equations 1 and 2 using values of $FiO_2$ or $FeO_2$ that correspond to the desired protection for the delivery of the safe non-hypoxic threshold concentration, and an estimated or assumed oxygen uptake (VO2). A typical safe threshold value for either $FiO_2$ or $FeO_2$ is 25%. It can be seen from equation 1 that the relationships of the variables are independent of the ventilator parameters. As such, $FeO_2$ works well to establish the safe non-hypoxic delivery to the patient. Since $FiO_2$ is conventionally measured to alarm on hypoxic delivery, the safe $FiO_2$ goals are familiar to operating clinicians and technicians, thus, it is useful in embodiments to use the $FiO_2$ as a safe non-hypoxic gas concentration threshold for gases delivered to the patient. Depending upon the combination of inputs being made by the clinician in the input device 54 (e.g. FGF and. $FFGO_2$, or $FGO_2F$ and BGF) the DSP 36 calculates the threshold value of the parameter being set using the current value of the complementary parameter. The safe input threshold values are the minimum oxygen concentration, the minimum oxygen flow, the minimum fresh gas flow rate, or the maximum balance gas flow rate.

Therefore, if the clinician attempts to enter a value for the fresh gas flow rate (FGF), then the DSP 36 calculates the minimum fresh gas flow rate using equations 1 and 2 using safe non-hypoxic $FiO_2$ or $FeO_2$ threshold concentration, patient oxygen uptake (VO2), and the current set value for the fresh gas oxygen concentration ($FFGO_2$). If the value of the fresh gas flow rate being set is higher than the minimum fresh gas flow rate, the DSP 36 will accept the setting being made, thus ensuring that the gas manifold 34 will be controlled to provide adequate oxygen to the patient 12. If the clinician attempts to input a value for the fresh gas oxygen concentration ($FFGO_2$), the DSP 36 calculates a minimum fresh gas oxygen concentration ($FFGO_2$) using equations 1 and 2 using safe non-hypoxic $FiO_2$ or $FeO_2$ threshold concentration, patient oxygen uptake (VO2), and the current set value for the fresh gas flow rate that must be provided by the fresh gas manifold 34 to provide adequate oxygen in the inspired gases 16 to the patient 12. Settings above the minimum fresh gas oxygen concentration are values that the DSP 36 will accept as safe non-hypoxic values to control the fresh gas manifold 34. As a minimum provision, the clinician should be alerted to a hypoxic setting is attempted.

The relationship between fresh gas flow rate (FGF), balance gas flow rate (BGF), fresh gas oxygen flow rate ($FGO_2F$), and anesthetic agent vapor flow rate (AVF) can be determined by the following equation:

$$FGF = BGF + FGO_2F + AVF \quad (7)$$

Additionally, combining equation (5) with equations (1) through (4), DSP 36 can calculate the safe non-hypoxic range of $FGO_2F$, BGF, and AVF settings to control the gas manifold 34. In this complementary pair of fresh gas manifold settings, if the clinician attempts to input a setting value for the BGF, the DSP 36 calculates, using equations 1 through 5, values of safe non-hypoxic $FiO_2$ or $FeO_2$ threshold concentration, patient oxygen uptake (VO2), and the current set value for the $FGO_2F$, a maximum BGF that must not be exceeded to ensure that the fresh gas manifold 34 will be controlled to provide adequate oxygen to the patient 12. Only values that are below the maximum BGF will be accepted by the DSP 36 to control the delivery of gases from the fresh gas manifold 34. Settings above the minimum fresh gas oxygen concentration are values that the DSP 36 will accept as safe non-hypoxic values to control the fresh gas manifold 34. In one embodiment, the clinician is alerted when a hypoxic BGF setting is attempted. In a further embodiment, the DSP 34 uses a similar process when the clinician attempts to set the $FGO_2F$ to ensure that only safe non-hypoxic $FGO_2F$ settings above the minimum $FGO_2F$ is being set or (as a minimum requirement) alert the clinician of a hypoxic $FGO_2F$ setting is attempted.

While the above examples have been for single pairs of fresh gas manifold parameters, it is to be recognized that in alternative embodiments, the clinician may input or otherwise establish a plurality of fresh gas manifold parameters. In this case, the DSP 36 would calculate the required minimum or maximum values for the additional parameters with respect to the input values at the equations as described above. The addition of anesthetic vapor into the fresh gas line 46 by the anesthetic vaporizer 32 can be similarly treated as an additional parameter.

In a still further embodiment of the respiratory support system 10, a graphical display 66 is communicatively connected to the DSP 36. The graphical display 66 is operated by the DSP 36 in order to present information regarding the operation and settings of the respiratory support system 10. In an embodiment, when the clinician enters a ventilator parameter value into the input device 54, the DSP 36 determines if the modified ventilator parameter value will result in the delivery of a hypoxic gas mixture to the patient if the remaining fresh gas manifold or ventilator parameter settings remain unchanged. The determination is made by comparing a predicted delivered oxygen gas concentration to a minimal patient oxygen requirement threshold. If the DSP 36 determines that such a change to the ventilator parameter would result in a hypoxic gas mixture delivered to the patient, then the DSP 36 can reject the clinician's entry and produce an alarm, including a visual or audible alarm with the graphical display 66. In an embodiment, the graphical display 66 further presents a prompt or option to the clinician in order to override the alarm, such that the clinician may selectively and deliberately change the ventilator parameter value, despite the warning that such a change on its own will result in the delivery of a hypoxic gas to the patient.

Figure 2:
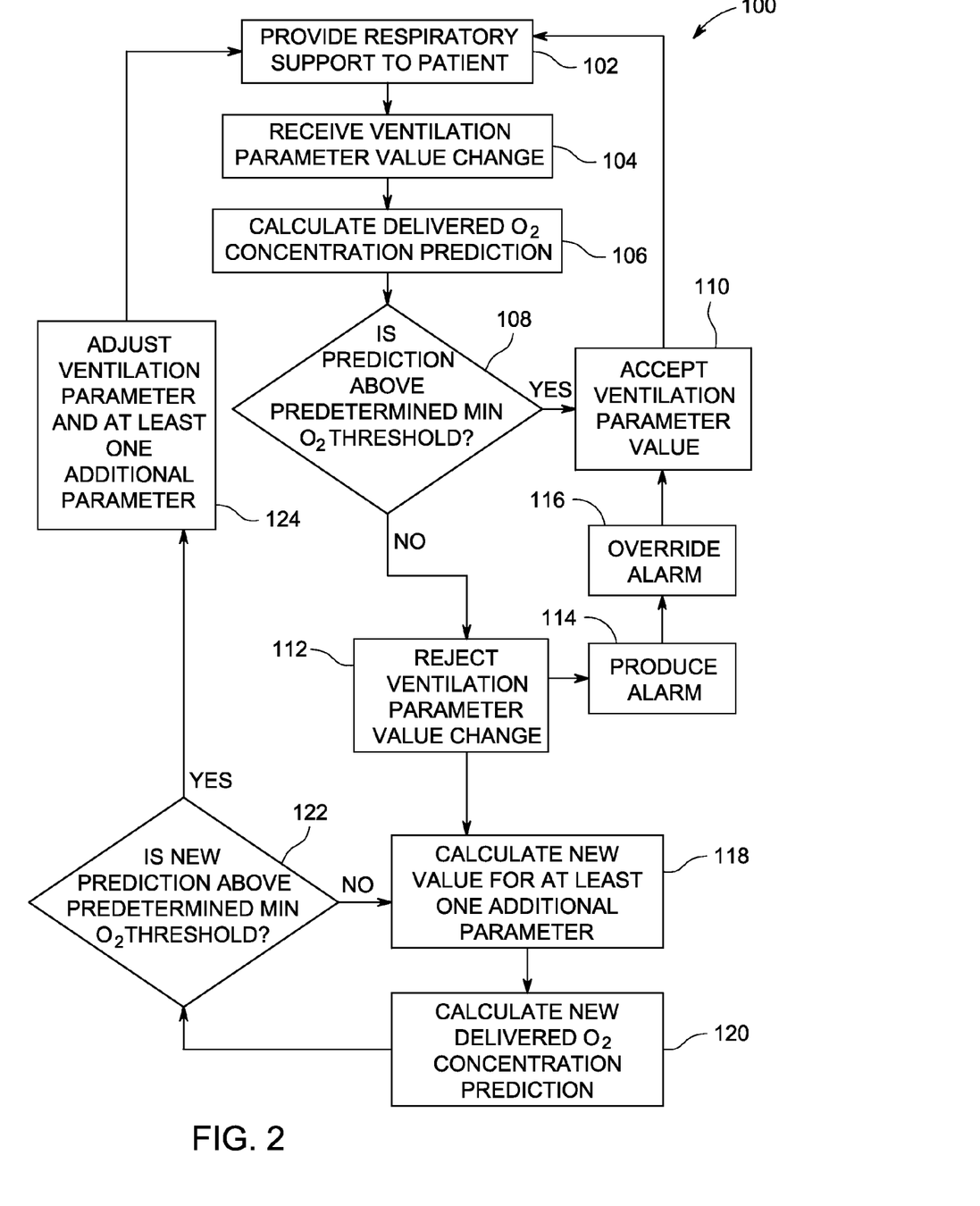
FIG. 2 is a flow chart that depicts an embodiment of a method of controlling the delivery of medical gases to a patient.

FIG. 2 is a flow chart that depicts an embodiment of a method of preventing the delivery of hypoxic gases to a patient. It is to be understood that embodiments of the method as disclosed herein with respect to FIG. 2 need not require each of the steps as detailed herein, nor specifically in the order described herein. Additionally, embodiments of the method may be performed solely through the use of a computer that executes computer readable code stored on a computer readable medium. The technical effect of such embodiments would be to prevent the delivery of hypoxic gases to a patient. Other embodiments of the method may be performed with a respiratory support system such as, but not limited to that depicted and disclosed in FIG. 1.

The method 100 starts with respiratory support being provided to the patient at 102. The respiratory support provided at 102 can either be full mechanical ventilation or can be spontaneous breathing assistance. Additionally, the respiratory support may include the delivery of anesthetic agent or other gaseous or nebulized drugs entrained in the medical gas delivered to the patient.

At 104, a ventilation parameter change is received by a digital signal processor (DSP). In one embodiment, the ventilation parameter value change is received by a clinician entering a change in the ventilation parameter value through an input device. In an alternative embodiment, the ventilation parameter value change is received from an automated fresh gas manifold control system, or as part of a plurality of ventilation parameter value changes. In embodiments, the ventilation parameter value changed by the clinician includes, but is not limited to, FGF, $FFGO_2$, MV, $FGO_2F$, and BGF. A person of ordinary skill in the art would recognize alternative ventilation parameter values that may additionally or alternatively be used in embodiments of the systems and methods as disclosed herein.

The DSP digital signal processor calculates a prediction of the oxygen concentration that will be delivered to the patient at 106 if the ventilation parameter value change is made. As described above with respect to FIG. 1, the calculated delivered oxygen concentration prediction can be calculated using one or more equations as disclosed above that relate the concentration and flow rate of expired gases from the patient and the fresh gas supply to the concentration and flow rate of inspiratory gases provided to the patient.

At 108, the predicted oxygen concentration is compared to a predetermined threshold that is representative of a minimal oxygen metabolic need of the patient. The patient's metabolic oxygen need, or oxygen uptake can be supplied to the digital signal processor in a variety of ways. In some embodiments, the patient oxygen uptake is measured directly or calculated from inspired gas and expired gas oxygen concentration values. Alternatively, a population or other demographic estimate of oxygen need can be used as a substitute for a measured or derived value that would be more patient specific.

If the predicted delivered oxygen concentration is above the predetermined minimum of oxygen concentration threshold, then at 110, the digital signal processor accepts the ventilation parameter value to the value that had been received at 104. The method 100 continues back to 102 where respiratory support is provided to the patient with the new and updated ventilation parameter value.

If the predicted delivered oxygen concentration does not meet the predetermined minimum oxygen concentration threshold, then at 112, the digital signal processor rejects the ventilation parameter value change that was received at 104.

In one embodiment, after the ventilation parameter value change has been rejected at 112, the digital signal processor operates a graphical display or other output device to produce an alarm at 114. The alarm produced at 114 serves to notify the clinician that a hypoxic gas mixture would be delivered to the patient if the ventilation parameter value from 104 were accepted. The alarm may further include a prompt for the clinician to override the alarm. At 116, a signal to override the alarm is received. A clinician may enter such an override signal through an input device. This feature or control may be desired by a clinician in an event wherein the clinician has particular knowledge of the specific respiratory therapy or condition of the patient. Therefore, the clinician specific knowledge can be implemented and the clinician can override the alarm to deliver the respiratory support according to the ventilation parameter value input by the clinician. After the alarm is overridden at 116, the ventilation parameter is accepted at 110 and respiratory support is provided to the patient according to the new ventilation parameter value.

Alternatively, after the digital signal processor rejects the ventilation parameter change at 112, the DSP calculates a new value for at least one additional parameter at 118. The DSP calculates at least one additional parameter value change that would be required to accept the input ventilation parameter value change and still prevent the delivery of a hypoxic gas mixture to the patient. In one embodiment, this is performed through an iterative process wherein a new value for at least one additional parameter is used to calculate a new delivered oxygen concentration prediction at 102. The new delivered oxygen concentration prediction is compared to the predetermined threshold at 122. If the new delivered oxygen concentration prediction is still below the threshold, then a new value for the at least one additional parameter is calculated at 118 and the loop repeats. Non-limiting examples of additional parameter values that are changed include the fresh gas oxygen concentration ($FFGO_2$) and the fresh gas flow rate (FGF).

If the new delivered oxygen concentration prediction based upon the received ventilation parameter value and the at least one additional parameter value is above the predetermined threshold at 122, than at 124 the DSP accepts the ventilation parameter value and the at least one additional parameter value. Respiratory support is then provided to the patient using the new ventilation parameter value and at least one additional parameter value.

The inventors have observed that some clinicians have had difficulty in adopting ventilation control and anesthesia delivery techniques to maximize the benefits gained from low-flow respiratory support systems. Exemplarily, a clinician may inefficiently use a low-flow respiration support system operating at a fresh gas flow of two or three liters per minute when the low-flow respiratory support system has the capability to safely provide respiratory support at flows of 500 milliliters per minute or less. The methods and systems as disclosed herein can further be leveraged to assist clinicians in more efficiently using the capability of the low-flow respiratory support system by providing additional information and feedback so that the clinician can self-correct.

Figure 3:
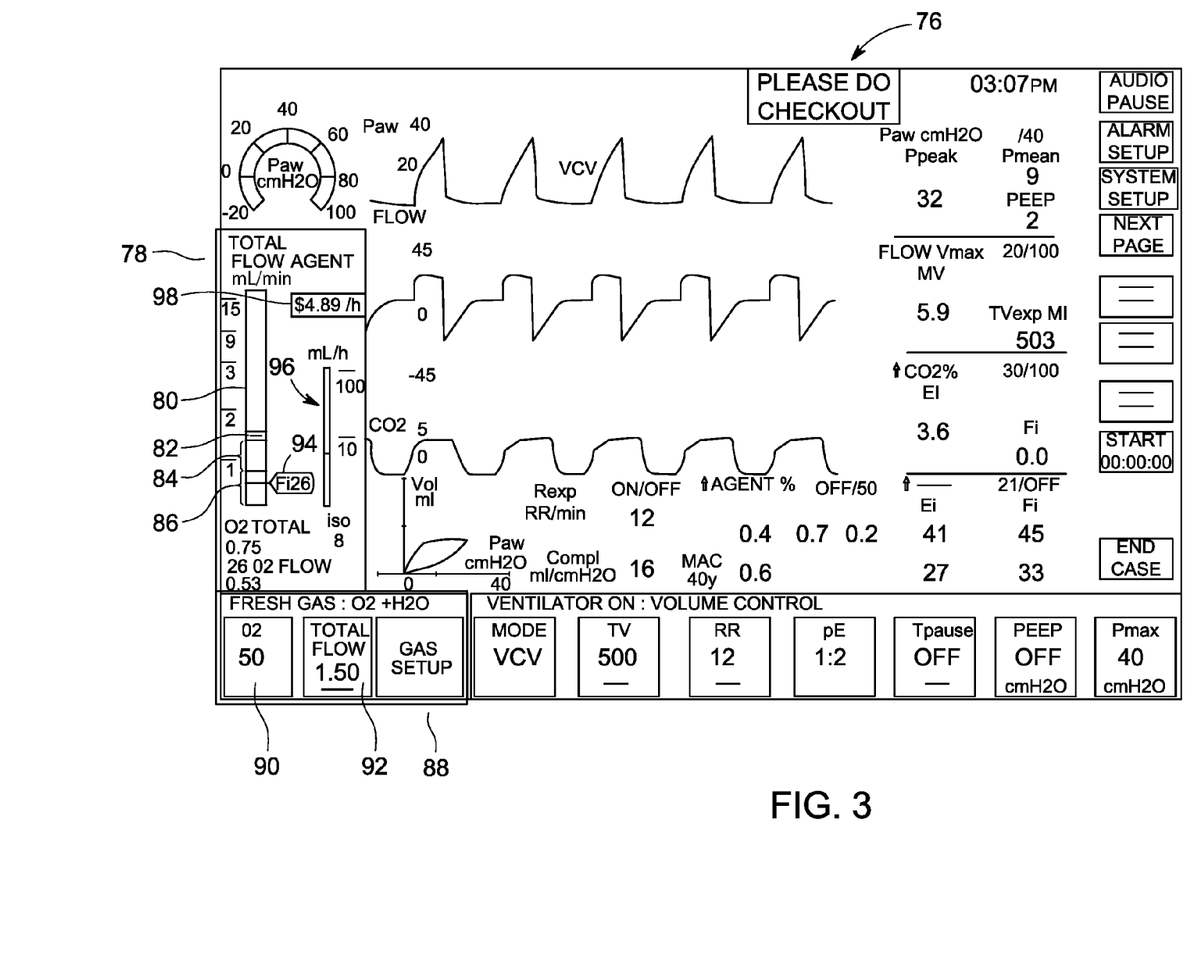
FIG. 3 depicts an example of a screen shot of an embodiment of a graphical user interface.

FIG. 3 depicts an example of a screen shot of an embodiment of a graphical user interface as may be presented on graphical display 66 (FIG. 1). The graphical user interface (GUI) 76 presents a variety of information related to the provision of ventilatory assistance and the delivery of anesthetic agent to the patient. The GUI 76 includes region 78, which may be a separate graphical user interface, or a subordinate graphical interface to the larger GUI 76. Region 78 includes a total flow graph 80. The total flow graph 80 graphically presents the flow of constituent gases exiting the mixer 70 of the respiratory support system 10 (FIG. 1). In the embodiment of the total flow graph 80 as depicted in FIG. 3, the top bar 82 represents the total flow rate (exemplarily expressed as a rate in liters per minute) of fresh gas out of the mixer. In an embodiment, the top bar 82 graphically depicts a bobbin or float as traditionally used in mechanical meters of medical gas flow.

Below the top bar 82 are two regions: a balance gas region 84 and an oxygen region 86. Both of these regions respectively graphical indicate the flow rates of these two components to the total fresh gas flow. As will be explained in further detail herein, fresh gas flow out of the mixer includes an oxygen component comprising the oxygen from air supplied to the mixer as well as supplemental oxygen provided from an oxygen source. The remainder of the total fresh gas flow can be considered a balance gas making up the remainder of the total flow graph 80. In embodiments, this also includes the component attributable to anesthetic agent vapor. By superimposing the oxygen flow rate as the oxygen region 86 over the flow rate of all the fresh gas, the total flow graph 80 also represents the concentration of oxygen in the fresh gas supplied by the mixer.

The graphical user interface 76 can further include an additional region or subordinate graphical user interface 88 that includes control buttons or icons such as to select and confirm settings for the fresh gas supplied from the mixer. Exemplarily, an oxygen concentration button 90 and a total flow button 92 are depicted in the region 88. By entering a change to the oxygen concentration or to the total flow rate with the respective buttons 90, 92, the total flow, and resulting oxygen flow component represented in the total flow graph 80 will change accordingly, as explained above with respect to equation 5.

The region 78 further includes a delivered oxygen reference 94. As explained above and detailed further herein, an oxygen concentration as delivered to the patient can be calculated from various measurements and inputs in the respiratory support system, particularly by application of equation 1. In a further manner of leveraging this technology, a value for an oxygen flow rate that achieves a predetermined referenced oxygen concentration as delivered to the patient can be calculated and superimposed as the delivered oxygen reference 94 on the total flow graph 80. Therefore, the delivered oxygen reference 94 provides further guidance to a clinician such that a reference oxygen concentration as delivered is presented based upon the oxygen flow rate out of the mixer that achieves the delivery of that oxygen concentration to the patient at the current total fresh gas flow rate out of the mixer.

The region 78 further includes an anesthetic agent flow graph 96. The anesthetic agent flow is determined as disclosed in further details herein, and is presented, exemplarily at a rate of milliliters (mL) per hour in the anesthetic agent flow graph 96. As further described herein, the anesthetic agent flow rate can be converted into an anesthetic agent cost estimate 98 that is presented in the region 78. In the example provided in FIG. 3, the anesthetic agent cost estimate is further presented as a rate, exemplarily dollars per hour. Details of the graphical user interface 76 and the determination and presentation of the values described above are explained in further detail herein, particularly with respect to the flow chart of FIG. 4.

Figure 4:
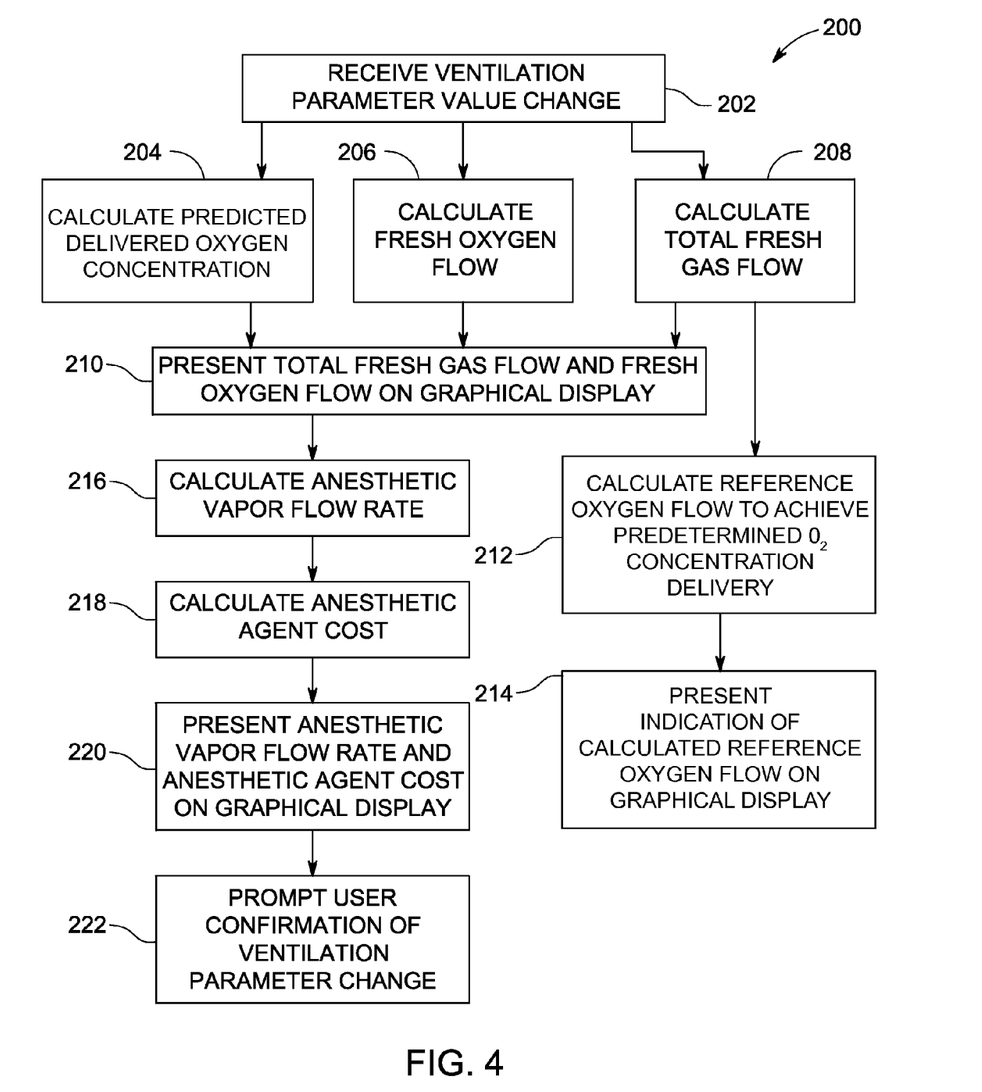
FIG. 4 is a flow chart that depicts an embodiment of a method of controlling the delivery of medical gases.

FIG. 4 is a flow chart that depicts an embodiment of a method of controlling the delivery of medical gases 200. The method 200 depicted in FIG. 4 includes similarities to portions of the flow chart depicted in FIG. 2, and it is understood that in embodiments, both methods 100 (FIG. 2) and 200 (FIG. 4) may be conducted concurrently. At 202, similar to step 104 in FIG. 2, a ventilation parameter value change is received. As mentioned above, the change to the ventilation parameter value can be any of a variety of changes to a variety of ventilation parameter values, including, but not limited to FGF, FFGO$_2$, MV, FGO$_2$F, and BGF. In other embodiment, the received ventilation parameter change can include anesthetic agent vapor flow rate (AVF). In still further embodiments, the received ventilation parameter change can be an updated measured value of any of the above parameters, or another ventilation parameter value as would be recognized by one of ordinary skill during the course of operation of the respiratory support system.

After the method 200 is initiated with the receipt of a ventilation parameter value change at 202, then one or more of 204, 206, and 208 are performed in order to calculate one or more values needed to carry out the method 200. It is to be understood that if the received ventilation parameter value change at 202 is one of the values calculated at 204, 206, or 208, such calculations result in the received ventilation parameter value from 202.

At 204, the predicted delivered oxygen concentration to the patient is calculated such as explained above with respect to FIGS. 1 and 2 and particularly using equation (1). At 206 a fresh oxygen flow rate into the breathing circuit is calculated. At 208 the total fresh gas flow rate into the breathing circuit is calculated. The relationship between the fresh oxygen flow and the total fresh gas flow is discussed above with respect to equation 7.

At 210 the total fresh gas flow from 208 and the fresh oxygen flow from 206 are presented on a graphical display. An exemplary embodiment of such a presentation is depicted in FIG. 3. As described above with respect to FIG. 3, the fresh oxygen flow can be presented as superimposed on top of the total fresh gas flow such that the concentration of oxygen in the fresh gas flow into the breathing circuit is further also graphically represented. It can also be recognized that in alternative embodiments, the concentration of oxygen in the fresh gas flow is calculated at 206, rather than the flow rate of oxygen in the fresh gas flow as these values are mathematically related and indicative of the same system properties of the fresh gas flow entering the breathing circuit.

At 212 a reference oxygen flow into the breathing circuit required to achieve a predetermined oxygen concentration delivery to the patient is calculated from at least the total fresh gas flow from 208. This is a further leveraging of the equations as explained above wherein at 212 the reference oxygen flow to achieve the delivery of a predetermined oxygen concentration is calculated in the same manner as described above with respect to equations 1-2; however, in some embodiments of 212, the predetermined oxygen concentration need not be a minimum oxygen concentration (nominally 21%), but may be another reference concentration value such as to assist a clinician in selecting the ventilation parameter value, or a high reference oxygen concentration such as to prevent oxygen toxicity. Non-limiting examples of the predetermined oxygen concentration delivered to the patient may include 25% oxygen or 30% oxygen although these examples are not intended to be limiting on the predetermined oxygen concentrations used at 212. If the reference is a high reference to warn of oxygen toxicity, the predetermined concentration may exemplarily be 90%. As noted above, general anesthesia practice would generally recommend that the predetermined oxygen concentration not be below the 21% oxygen found in air, below which would constitute a hypoxic mixture and, as such, may be desired to be avoided.

After the reference oxygen flow is calculated at 212 an indication of the calculated reference oxygen flow into the breathing circuit required to deliver the predetermined oxygen concentration to the patient is presented on the graphical display 214. In one embodiment as depicted in FIG. 3, the indication of the calculated reference oxygen flow is presented as a reference tab on the total flow graph that is labeled with the predetermined oxygen concentration delivered to the patient, but represents the fresh oxygen flow rate into the breathing circuit that is required to achieve the delivery that predetermined oxygen concentration to the patient.

In mechanically actuated vaporizers, neither the anesthetic concentration setting nor the vapor flow rate are electronically measured but can be calculated from at least one variable from the ventilator and the respiratory gas monitor connected to the patient. At 216 an anesthetic vapor flow rate (AVF) is calculated. The calculation of the anesthetic vapor flow rate is calculated in a similar manner to that described above with respect to the calculation of the oxygen as delivered to the patient. The anesthetic vapor flow rate is calculated based upon one of two equations depending upon whether the expired minute volume (MVe) is greater than or less than the total fresh gas flow provided by the mixer (FGF). If the MVe is greater than or equal to FGF, then the anesthetic agent vapor flow rate is calculated by:

$$AVF(mL/min) = \frac{FiA \cdot MVi - FeA \cdot MVe - FGF}{1 - FeA} \quad (8)$$

If the MVe is less than the FGF, then the anesthetic flow rate is calculated by:

$$AVF(mL/min) = \frac{FiA \cdot FGF}{1 - FiA} \quad (9)$$

It is to be noted that in the above equations 6 and 7, if the MVe is greater than the inspired minute volume (MVi), the MVe value is set equal to the MVi value. The above equations 8 and 9 use the fraction of agent inspired (FiA) and fraction of agent expired (FeA) in calculating the rate per minute at which the anesthetic agent vapor is delivered. It is to be noted that if AVF is desired to be represented at an alternative rate, exemplarily millimeters per hour as depicted in FIG. 3, then the above equations 8 and 9 would include the appropriate conversation, exemplarily multiplying by 60 minutes per hour. The FiA and FeA values used in equations 8 and 9 may be calculated or obtained from the vaporizer system that measures the amount of anesthetic agent that is being metered out through the vaporizer. In a still further embodiment, the anesthetic vapor flow rate may be measured directly from a gas analyzer disposed in the breathing circuit.

After the anesthetic vapor flow rate is calculated at 216, the cost of the anesthetic agent cost consumed to supply the anesthetic vapor flow is calculated at 218. In order to first estimate the cost of the anesthetic agent being used, the anesthetic vapor flow rate (AVF) must be converted to a liquid agent flow rate. This is calculated using equation 10:

$$ALF = \frac{AVF}{\text{CONVERSION FACTOR}} \quad (10)$$

In equation 8 the liquid anesthetic flow (ALF) is calculated by dividing the anesthetic vapor flow by a conversion factor. Exemplary conversion factors are provided in the following table.

| Anesthetic Agent | Conversion Factor |
| --- | --- |
| desflurane | 208 |
| enflurane | 198 |
| halothane | 227 |
| isoflurane | 196 |
| sevoflurane | 181 |

As shown in the Table above, the conversation factors are specific to the anesthetic agent and convert the vapor flow rate of the anesthetic agent into a liquid flow rate as anesthetic agents are typically sold and priced in their liquid form. The hospital or institution may enter a current cost associated with each anesthetic agent that may be used by the respiratory support system and the estimated anesthetic agent cost is calculated at 218 by multiplying the anesthetic agent cost by the liquid anesthetic agent flow rate to arrive at a cost per unit of time that the anesthetic agent is provided at that rate. It is understood that the estimated anesthetic agent cost can be localized to the country or region in which the respiratory support system is used by changing the currency or cost per volume references in the estimated anesthetic agent cost.

At 220, the anesthetic vapor flow rate and anesthetic agent cost are both presented on the graphical display. As referenced above, this is exemplarily depicted in FIG. 3 by the anesthetic agent flow graph 96 and the anesthetic agent cost estimate 98. It is to be noted that the anesthetic agent cost estimate is presented in a rate of dollars per hour, but as disclosed above, this can be localized.

In some embodiments of the method 200, at 222 the presentations of information reflecting the ventilatory and anesthesia support to be provided to the patient particularly from 210, 214, and 220 within the method provide the clinician with additional insight and guidance as to the respiratory support to be provided and the user or clinician is prompted to confirm the entered ventilation parameter change after being informed of the effects of that change by the presentation as herein just described. It is to be noted that in other embodiments, the ventilation parameter value change may be implemented by the respirator support system as soon as the parameter value change is received at 202, in such embodiments, the method 200 may be carried out in real time, continuously representing the actual conditions of the respiratory support provided to the patient.

As noted above, an anesthesiologist or other clinician may use greater flow rates of fresh gas and anesthetic agent than are required by modern low flow respiratory systems. Part of this may stem from caution, or may be a result of clinicians being inexperienced with extent of the flow capabilities of low flow ventilatory support systems. By visually presenting the clinician with this information, the clinician can see that equivalent respiratory support can be provided at lower fresh gas and anesthetic agent consumption rates. Such changes in operation can result in reduced cost of ownership and wasted medical gas and anesthetic agent.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system for controlling the delivery of medical gases to a patient, the system comprising:
    a breathing circuit including a patient connection;
    a mixer pneumatically connected to the breathing circuit, the mixer receives at least oxygen and a balance gas and provides a combined gas comprising at least oxygen and the balance gas to the breathing circuit;
    a digital signal processor communicatively connected to the mixer, the digital signal processor receives at least one ventilation parameter value change, calculates a fresh oxygen flow rate into the breathing circuit and a total fresh gas flow rate into the breathing circuit with the at least one ventilation parameter value, and calculates a reference oxygen flow rate representative of a predetermined oxygen concentration delivered to the patient with at least the total fresh gas flow rate; and
    a graphical display communicatively connected to the digital signal processor, wherein the graphical display presents the calculated fresh oxygen flow rate, the total fresh gas flow rate, and the reference oxygen flow rate.

2. The system of claim 1, further comprising:
    a mechanical ventilator pneumatically connected to the breathing circuit, the mechanical ventilator configured to create fluid pressure waveforms within the breathing circuit to provide respiratory support to the patient; and
    an input device operable by a clinician to input the at least one ventilation parameter change.

3. The system of claim 1, further comprising:
    a vaporizer pneumatically connected to the breathing circuit;
    wherein the digital signal processor calculates an anesthetic agent consumption rate at least in part from the total fresh gas flow rate, calculates an estimated cost from the anesthetic agent consumption rate, and operates the graphical display to present the estimated cost.

4. The system of claim 3, wherein the digital signal processor calculates an anesthetic vapor flow rate based upon the difference of the fresh gas flow rate and a product of a fraction of expired agent and an expired minute volume from a product of a fraction of inspired agent and an inspired minute volume and the digital signal processor operates the graphical display to present the calculated anesthetic vapor flow rate.

5. The system of claim 3, wherein the digital signal processor calculates the anesthetic vapor flow rate based upon a product of a fraction of inspired agent and the fresh gas flow rate and the digital signal processor operates the graphical display to present the calculated anesthetic vapor flow rate.

6. The system of claim 1, wherein the predetermined oxygen concentration is a predetermined hypoxic concentration threshold.

7. The system of claim 1, further comprising:
    a respiratory gas monitor pneumatically connected to the breathing circuit, the respiratory gas monitor produces signals indicative of an oxygen concentration inhaled and exhaled by the patient;
    wherein the digital signal processor calculates the predetermined minimum oxygen requirement threshold using at least one of the signals indicative of oxygen concentration inhaled and exhaled by the patient.

8. A ventilation system that provides respiratory support to a patient, the system comprising:
    a breathing circuit with a patient connection;
    an input device operable by a clinician to input at least one ventilation parameter value;
    a mixer pneumatically connected to the breathing circuit, the mixer receives at least oxygen and a balance gas and provides a combined gas comprising at least oxygen and the balance gas to the breathing circuit;
    a digital signal processor communicatively connected to the input device, the digital signal processor receives the at least one ventilation parameter value, calculates a fresh oxygen flow rate into the breathing circuit, calculates total fresh gas flow rate into the breathing circuit, calculates a predicted oxygen concentration delivered to the patient, and compares the predicted oxygen concentration to a predetermined minimum oxygen requirement threshold of the patient; and
    a graphical display communicatively connected to the digital signal processor, the graphical display presents the calculated fresh oxygen flow rate and total fresh gas flow rate;
    wherein if the predicted oxygen concentration is above the predetermined minimum oxygen requirement threshold, the digital signal processor accepts the at least one ventilation parameter value.

9. The system of claim 8, wherein if the predicted oxygen concentration delivered to the patient is below the predetermined minimum oxygen requirement threshold, the digital signal processor calculates at least one additional parameter value such that the predicted oxygen concentration is above the predetermined minimum oxygen requirement threshold, and the digital signal processor accepts the at least one ventilation parameter value and at least one additional parameter value.

10. The system of claim 8, further comprising:
    a vaporizer pneumatically connected to the breathing circuit;
    wherein the digital signal processor further calculates a predicted anesthetic vapor flow rate at least in part from the total fresh gas flow rate, the digital signal processor further converts the predicted anesthetic vapor flow rate to an anesthetic agent consumption cost and the graphical display presents the anesthetic agent consumption cost.

11. The system of claim 10, further comprising:
a respiratory gas monitor pneumatically connected to the breathing circuit, the respiratory gas monitor produces signals indicative of at least an anesthetic agent concentration inhaled exhaled by the patient;
wherein the digital signal processor calculates the anesthetic vapor flow rate from at least the indicated inhaled and exhaled anesthetic agent concentrations and the total fresh gas flow rate.

12. The system of claim 8, wherein the digital signal processor calculates an anesthetic vapor flow rate based upon a difference of the fresh gas flow rate and a product of an exhaled anesthetic agent concentration and an exhaled minute volume from a product of an inhaled anesthetic agent concentration and an inhaled minute volume and the digital signal processor operates the graphical display to present the calculated anesthetic vapor flow rate.

13. The system of claim 8, wherein the digital signal processor calculates an anesthetic vapor flow rate based upon a product of an inspired anesthetic agent concentration and the fresh gas flow rate, and the digital signal processor operates the graphical display to present the calculated anesthetic vapor flow rate.

14. A method of controlling the delivery of medical gases to a patient receiving ventilatory support from a low-flow mechanical ventilator, the method comprising:
providing ventilatory support to the patient through a breathing circuit pneumatically connected to the low-flow mechanical ventilator;
receiving, with a mixer pneumatically connected to the breathing circuit, a flow of medical gas comprising oxygen;
receiving, with a digital signal processor, a ventilation parameter value change;
calculating, with the digital signal processor and based upon the received ventilation parameter value change, at least one of:
a total fresh gas flow rate into the breathing circuit; and
a fresh oxygen flow rate into the breathing circuit; and
presenting the total fresh gas flow rate, and the fresh oxygen flow rate on a graphical display.

15. The method of claim 14, further comprising:
calculating, with the digital signal processor, a reference oxygen flow rate into the breathing circuit that achieves a predetermined oxygen concentration as delivered to the patient based upon the total fresh gas flow rate; and
presenting the reference oxygen flow rate into the breathing circuit on the graphical display.

16. The method of claim 14, further comprising:
calculating a predicted oxygen concentration delivered to the patient with the digital signal processor based upon the ventilation parameter value change;
comparing the predicted oxygen concentration to the predetermined oxygen concentration with the digital signal processor;
accepting, with the digital signal processor, the ventilation parameter value if the predicted oxygen concentration is above the predetermined oxygen concentration; and
rejecting, with the digital signal processor, the ventilation parameter value if the predicted oxygen concentration is below the predetermined oxygen concentration.

17. The method of claim 14, further comprising:
providing anesthetic agent from a vaporizer to the patient through the breathing circuit;
obtaining an expired minute volume; and
comparing the expired minute volume to the fresh gas flow rate.

18. The method of claim 17 wherein the expired minute volume is greater than or equal to the fresh gas flow rate and further comprising:
calculating an anesthetic agent vapor flow rate provided by the vaporizer based upon a difference of the fresh gas flow rate and a product of an exhaled anesthetic agent concentration and an exhaled minute volume from a product of an inhaled anesthetic agent concentration and an inhaled minute volume; and
presenting the calculated anesthetic agent vapor flow rate on the graphical display.

19. The method of claim 17 wherein the expired minute volume is less than the fresh gas flow rate and further comprising:
calculating an anesthetic agent vapor flow rate provided by the vaporizer based upon a product of an inspired anesthetic agent concentration and the fresh gas flow rate; and
presenting the calculated anesthetic agent vapor flow rate on the graphical display.

20. The method of claim 17, further comprising:
calculating an anesthetic agent vapor flow rate provided by the vaporizer based at lease upon a product of an inspired anesthetic agent concentration and the fresh gas flow rate;
presenting the calculated anesthetic agent vapor flow rate on the graphical display;
calculating, with the digital signal processor, an equivalent cost for the consumed anesthetic agent based upon the anesthetic agent vapor flow rate; and
presenting the calculated equivalent cost on the graphical display.

* * * * *